US008227659B2

(12) United States Patent
Toro et al.

(10) Patent No.: US 8,227,659 B2
(45) Date of Patent: Jul. 24, 2012

(54) LIQUID ABSORBING MATERIAL AND METHOD FOR MAKING THE SAME

(75) Inventors: Carlo Toro, Cepagatti (IT); Enzo Pompei, Pescara (IT); Giovanni Carlucci, Chieti (IT); Maurizio Tamburro, Sambuceto (IT)

(73) Assignee: The Procter & Gamble Company, Cincinnati, OH (US)

( * ) Notice: Subject to any disclaimer, the term of this patent is extended or adjusted under 35 U.S.C. 154(b) by 590 days.

(21) Appl. No.: 11/499,319

(22) Filed: Aug. 4, 2006

(65) Prior Publication Data

US 2007/0032566 A1     Feb. 8, 2007

(30) Foreign Application Priority Data

Aug. 5, 2005   (EP) .................................... 05017146

(51) Int. Cl.
*A61F 13/15*   (2006.01)
*A61F 13/20*   (2006.01)

(52) U.S. Cl. .......................... 604/367; 604/375; 604/376
(58) Field of Classification Search .................. 604/365, 604/367–369, 374–376
See application file for complete search history.

(56) References Cited

U.S. PATENT DOCUMENTS

| 2003/0045198 A1* | 3/2003 | Tanaka et al. ................ 442/417 |
| 2003/0109628 A1 | 6/2003 | Bonfanti et al. |
| 2004/0058159 A1 | 3/2004 | Gagliardi et al. |

FOREIGN PATENT DOCUMENTS

| EP | 0 157 960 A1 | 10/1985 |
| EP | 1 013 291 B1 | 6/2005 |
| WO | WO 98/27559 | 6/1998 |
| WO | WO 99/57201 | 11/1999 |
| WO | WO 03/049777 A1 | 6/2003 |
| WO | WO 2004/028427 A1 | 4/2004 |

OTHER PUBLICATIONS

Material Safety Data Sheet for Polyethylene Glycol, Jan. 9, 2006.*
PCT International Search Report dated Dec. 21, 2006

* cited by examiner

*Primary Examiner* — Michele M Kidwell
(74) *Attorney, Agent, or Firm* — Andres E. Velarde

(57) ABSTRACT

An improved material for liquid absorption including an absorbent material in particle form with a very low average particle size dispersed into a selected inert hydrophilic organic carrier which is solid at room temperature. The present invention also includes an improved process for manufacturing the material. Such liquid absorbing material can be utilized in the absorbent cores of disposable absorbent articles, such as sanitary napkins, panty liners, interlabial devices, tampons, disposable diapers, incontinence pads, wound dressings, nursing pads, and the like.

10 Claims, No Drawings

LIQUID ABSORBING MATERIAL AND METHOD FOR MAKING THE SAME

FIELD OF THE INVENTION

The present invention relates to a liquid absorbing material comprising a particulate absorbent material dispersed into a carrier. Such materials can be utilized in a number of end uses where liquid absorption is desired, for example liquid absorbing materials can be used in the absorbent core of disposable absorbent articles, such as sanitary napkins, panty liners, interlabial devices, tampons, disposable diapers, incontinence pads, wound dressings, nursing pads, and the like.

BACKGROUND OF THE INVENTION

In general the absorption and retention of aqueous liquids, particularly body fluids such as urine, menses, etc., are accomplished by use of absorbent articles containing absorbent materials. Such articles include sanitary napkins, panty liners, interlabial devices, tampons, disposable diapers, incontinence pads, wound dressings, nursing pads, and the like. Generally, the most used absorbent materials are cellulose materials (e.g., defiberised wood pulp) and superabsorbent materials. In particular, when referring to disposable diapers or sanitary napkins and the like presently available in the market, the cellulose materials are typically in the form of bat or sheet, and generally further contain particulate absorbent materials, usually referred to in the art as superabsorbents or hydrogelling materials, which allow to manufacture thin but very absorbent core structures. A primary reason to incorporate superabsorbent material in particle form within an absorbent structure is its stabilization, in order to counteract the tendency of powdered material to bunch up or agglomerate, hence providing an uneven absorptive capacity in the absorbent structure, or also to dust off the structure itself. Known approaches are for example to adhesively fix the particles into a fibrous structure, or to disperse the powdered superabsorbent material in a fibrous matrix, e.g., cellulose pulp, and fix it in place mechanically, e.g., by calendaring or embossing. An alternative approach is to blend a superabsorbent particulate material into a thermoplastic matrix, e.g., a thermoplastic composition. The superabsorbent containing thermoplastic composition can be typically extruded or coated in any desired position and pattern onto a suitable substrate, to be then incorporated into an absorbent article, thus entirely providing the absorbent material in the article, or alternatively integrating a more traditional fibrous absorbent structure, with no risk of dust off of the particulate material, or displacement within the absorbent structure of the article. For example, EP 1013291 and WO 98/27559 describe a hot melt adhesive containing a superabsorbent polymer. WO 99/57201 illustrates compositions comprising a thermoplastic component and a superabsorbent polymer, the compositions in form of a film layer or applied to a disposable absorbent article with various hot melt adhesive application techniques. Applications WO 03/049777 and WO 04/028427 describe thermoplastic compositions comprising a matrix of a thermoplastic polymeric composition and superabsorbent particles dispersed therein, which have a particularly effective fluid acquisition and handling capacity, and absorbent articles comprising superabsorbent containing thermoplastic compositions arranged in a pattern of unattached spaced apart zones.

The technology of composite thermoplastic materials comprising a matrix of a thermoplastic composition and particles of superabsorbent material dispersed therein has provided a solution to the problem of particulate or powdered superabsorbent material "instability" within absorbent structures in absorbent articles, preventing particle displacement as, e.g., dust-off, agglomeration, or bunching up, and safeguarding the end users of absorbent articles virtually from any undesired contact with the superabsorbent particles upon normal use.

However, composite thermoplastic materials comprising particles of superabsorbent materials are relatively complex to formulate, and moreover usually imply rather high temperatures when they are applied onto a substrate in the molten state, since typically the thermoplastic matrix is a hot melt adhesive. Care must be taken since some substrates can be heat sensitive. Also relatively high temperatures of the thermoplastic matrix in the molten state could negatively affect the particulate material itself, hence already in the manufacturing process of the composite thermoplastic material, as well as upon subsequent application onto a substrate.

According to an alternative approach as disclosed in EP 157960, the superabsorbent particles may be dispersed into a liquid carrier, for example an oil carrier, and applied onto a substrate as a liquid dispersion. However, a liquid dispersion is generally not preferred for application onto substrates since it is not stable. It can in fact spread or move onto, e.g., film substrates, particularly on substrates which are not wetted by the liquid carrier, or alternatively be absorbed into porous, typically fibrous, substrates, such as for example nonwoven or cellulose layers, migrating within the substrate and impregnating it, thus likely modifying the characteristics of the substrate itself. Moreover, particularly after application onto a substrate the particles of superabsorbent material dispersed into the carrier can still move and provide a non-homogeneous distribution within the carrier, and also interfere during the application process, for example clogging the extrusion die or nozzle.

An improvement can be the use of a particulate material having low average particle size, which is advantageous not only in terms of better, e.g., liquid handling and absorption capacity of a liquid absorbing material comprising said particles dispersed into a carrier, due to the increased surface/volume ratio provided by smaller particles, but also in an easier processability of the liquid absorbing material, which may have lower viscosities when prepared and/or applied to a substrate. Moreover, smaller average particle sizes allow preparation of a more homogeneous dispersion in the carrier.

However, powdered materials, for example typically superabsorbent materials, also pose health risks to those involved in the manufacturing process, particularly when they are manufactured in very small average particle sizes as mentioned above. The finely powdered superabsorbent material can become airborne and can be inhaled by workers. Once inhaled, the superabsorbent material absorbs liquid within the respiratory passages swelling to many time its original size. This can result in blocked air passages and potentially traumatic health complications.

Hence there is the need for an improved material for liquid absorption which is simpler to produce and to apply. There is also a need for such a material that provides improved stability after application onto a selected substrate. There is also a need to provide such a material that has compatibility towards most substrates, including heat sensitive substrates and various particulate absorbent materials. There is also the need for a simpler process for making such a material which eliminates the health and environmental problems related to the handling of particulate absorbent material in very low average particle size.

Accordingly, it would be desirable to provide an improved liquid absorbing material comprising a particulate absorbent material dispersed into a carrier, which has better absorption characteristics, and an increased stability and compatibility with a wide range of substrates.

It would also be desirable to provide an improved process for making such a material.

SUMMARY OF THE INVENTION

The present invention provides a liquid absorbing material comprising a particulate absorbent material and an inert hydrophilic organic carrier, where the particulate absorbent material is dispersed into the inert hydrophilic organic carrier. The particulate absorbent material has an average particle size of less than 40μ, and the inert hydrophilic organic carrier is solid at room temperature.

DETAILED DESCRIPTION OF THE INVENTION

By "liquid" as herein used is meant water based fluids or liquids such as urine, menses, serum, blood, sweat, mucous as well as other aqueous solutions generally defined as body fluids, but it is not intended to exclude other water based fluids.

By "room temperature" as herein used is conventionally meant a temperature of 25° C., as known in the art.

For purposes of the present invention, particle size is defined as the dimension of a particle which is determined by means of any suitable method known in the art for particle sizes comprised in the range according to the present invention. Particularly indicated are laser light scattering analysis or laser diffraction analysis. Reference is preferably made to the preferred method and apparatus for laser diffraction analysis described in the attached example. The average particle size of a given sample is defined as the particle size corresponding to a cumulative distribution of 50% of the particles of the sample. In other words, the average particle size of a given sample of absorbent material particles is defined as the particle size which divides the sample in half on a mass basis, i.e., half of the sample by weight will have a particle size greater than the average particle size and half of the sample by weight will have a particle size less than the particle size.

The liquid absorbing material of the present invention comprises an absorbent material in particulate form having a selected, low average particle size, which can be typically a water-insoluble, water-swellable absorbent material, or also a liquid gelling material, and an inert hydrophilic organic carrier which is solid at room temperature, wherein said particulate absorbent material is dispersed, typically homogeneously, into the inert hydrophilic organic carrier. In the context of the present invention, "inert", as referred to the hydrophilic organic carrier, is meant to indicate a hydrophilic organic carrier material which is substantially non-reactive with the absorbent material in particle form dispersed therein. According to a preferred embodiment of the present invention, the inert hydrophilic organic carrier is preferably selected among polyethylene glycol, polypropylene glycol, and derivatives thereof, which are solid at room temperature. The particulate absorbent material has an average particle size of less than about 40μ, less than about 30μ, between about 1μ and about 20μ, between about 10μ and about 20μ, or between about 10μ and about 15μ.

Particulate absorbent materials can be selected among known particulate water-insoluble, water-swellable absorbent materials or also particulate liquid gelling materials, in order to provide a liquid absorbing material according to the present invention.

Particulate water-insoluble water-swellable absorbent materials comprise known, typically crosslinked, absorbent materials which are usually referred to as "hydrogels", "super absorbents", "absorbent gelling materials" (AGM). Such materials, upon contact with aqueous fluids, especially aqueous body fluids, imbibe such fluids and thus form hydrogels by swelling of their own three-dimensional network provided by crosslinking. These absorbent materials are typically capable of absorbing large quantities of aqueous body fluids, and are further capable of retaining such absorbed fluids under moderate pressures. These absorbent materials are typically in the form of discrete, non fibrous particles, even if super absorbents in fibre form are known.

Any commercially available super absorbent material in particle form is suitable for the liquid absorbing material of the present invention. Suitable super absorbent materials for use herein will most often comprise a substantially water-insoluble, slightly crosslinked, partially or fully neutralized, polymeric gelling material. This material forms a hydrogel upon contact with water. Such polymer materials can be prepared from polymerizable, unsaturated, acid-containing monomers. Suitable materials are polyacrylate based superabsorbent polymers in particle form.

Particulate absorbent materials to be included in the liquid absorbing material of the present invention can also comprise particulate liquid gelling materials, which are materials, typically not crosslinked, which upon contact with liquid form a gel creating a three-dimensional network by interacting with the molecules present in the liquid, such as typically proteins, lipids, and so on in body fluids. Liquid gelling materials can be selected for example among polysaccharides, starches, modified cellulose. Suitable liquid gelling materials according to the present invention are cationic polysaccharides, including, but not limited to, chitosan and its derivatives, where the creation of a three-dimensional network upon contact with liquid, and hence gelification, is achieved by formation of electrostatic bonds between the positively charged cationic groups of the cationic polysaccharide and the negatively charged electrolytes contained in the fluid.

Suitable chitosan materials to be used herein include substantially water-soluble chitosan. Suitable chitosan materials for use herein may generally have a wide range of average molecular weights, typically ranging from about 1,000 to about 10,000,000, from about 2,000 to about 1,000,000. Particularly suitable chitosan materials for use herein are chitosan salts, particularly water-soluble chitosan salts. A variety of acids can be used for forming chitosan salts, namely inorganic and organic acids. Chitosan salts formed by the reaction of chitosan with an amino acid are also suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate and mixtures thereof. It is also suitable to form a chitosan salt using a mixture of acids including, for example, both inorganic and organic acids. One suitable chitosan salt for use herein is chitosan lactate.

The inert hydrophilic organic carrier according to the present invention can be selected among polyethylene glycols, polypropylene glycols, and derivatives thereof, such as for example polyoxymethylene glycols. Such hydrophilic organic carrier and the particulate absorbent material are selected such that the hydrophilic organic carrier is inert towards the particulate absorbent materials, i.e., does not substantially react with it, hence providing a true dispersion of the particulate absorbent material into the carrier. Polyethylene glycols, polypropylene glycols, and derivatives thereof are moreover highly hydrophilic, and hence have a good affinity with water and water based liquids, which is clearly advantageous for the final liquid absorbing material. The hydrophilic organic carrier upon contact with liquid promptly acquires and diffuses it and rapidly brings it in contact with the particulate absorbent material dispersed therein, which in turn can perform its liquid absorbing action with enhanced effectiveness.

According to the present invention, the inert hydrophilic organic carrier is solid at room temperature, hence has a melting point above the room temperature of 25° C., where, as it is known for polymers, the melting point is the DSC (Differential Scanning Calorimetry) melting point, which is the temperature identified as that corresponding to the DSC peak, or corresponding to the highest DSC peak in case of a mixture of polymers showing more than one peak. The inert hydrophilic organic carrier may have a melting point of at least about 40° C. and not more than about 110° C., between about 40° C. and about 90° C., or between about 50° C. and about 70° C.

When the inert hydrophilic organic carrier for the liquid absorbing material of the present invention is selected among polyethylene glycols, preferably the molecular weight is at least about 1200, between about 1200 and about 8000, between about 1500 and about 4000, or between about 1500 and about 2000.

The liquid absorbing material of the present invention comprising the inert hydrophilic organic carrier with the particulate absorbent material homogeneously dispersed therein can be prepared by simply heating the inert hydrophilic organic carrier to a temperature above its melting point, and by subsequently adding the particulate absorbent material, compounding and mixing in order to obtain a homogeneous dispersion of the particulate absorbent material into the carrier. The resulting material can be cooled and stored in solid state for further use, or directly applied to the selected substrate.

Application onto a substrate is performed with the material in liquid form, typically in the molten state by suitably heating the material to a temperature above the melting point of the organic carrier, and applying it onto the substrate in the desired pattern with known techniques, such as for example low temperature melt extrusion or melt coating. The selection of the organic carrier according to the present invention allows the use of low and very low application temperatures for the liquid absorbing material, usually below about 110° C., down to between about 50 and about 70° C., which makes the liquid absorbing material compatible with virtually any substrates, such as for example woven and nonwoven layers, thermoplastic film layers, tissue, paper, and so on, such as those commonly used in the manufacture of absorbent articles like sanitary napkins, panty liners, interlabial devices, tampons, disposable diapers, incontinence pads, wound dressings, nursing pads, and the like.

The low and very low melting points of the selected hydrophilic organic carriers are also compatible with almost any particulate absorbent material according to the present invention, which are typically not affected by such low temperatures of the carrier in the molten state both in the compounding and manufacturing process of the liquid absorbing material, and in the application of said material onto a substrate.

Moreover, the low and very low melting points of the selected hydrophilic organic carriers make both the manufacture and the application processes of the liquid absorbent or liquid gelling materials of the present invention simpler and less demanding in terms of energy and machinery. At the same time said materials, owing to the melting point of the selected organic carrier which is low yet above the room temperature, are solid after application onto the substrate and subsequent cooling, and in general during the life of the product, i.e., storage and use, and hence provide a greatly increased stability to the material itself into the product, since the material cannot impregnate or diffuse into the substrate, and more in general into the product after cooling and solidification.

In an alternative embodiment, the liquid absorbing material of the present invention can be prepared and/or applied onto a substrate in liquid state substantially at room temperature, by dissolving the hydrophilic organic carrier into a suitable solvent, which however should not interfere with the particulate absorbent material, such as for example a suitable organic solvent, and then adding and mixing the particulate absorbent material. Application onto a substrate can also be performed in solution, wherein solidification is subsequently achieved by withdrawal of the solvent with known means.

The liquid absorbing material of the present invention allows the incorporation in the final product, such as a liquid absorbent product, of the respective particulate absorbent materials having an extremely low average particle size, without the environmental and health problems implied by the handling of materials in form of fine and very fine particles, particularly the environmental and health problems related to the handling of particles of water-insoluble water-swellable absorbent material.

According to the present invention, the liquid absorbing material comprises a particulate absorbent material having an average particle size of less than about 40μ, less than about 30μ, between about 1μ and about 20μ, between about 10μ and about 20μ, between about 10μ and about 15μ, wherein the average particle size is measured as described herein.

The use of particulate absorbent material having a very low average particle size is generally advantageous in that it allows an easier processability of the liquid absorbing material comprising the particulate absorbent material. As it is known, addition of solid particles into a matrix of a liquid, namely molten, material increases the overall viscosity of the material in the liquid/molten state at given conditions, when compared with the viscosity of the same material without particles, at the same conditions. Selection of particles having a preferred low or very low average size reduces this effect, providing a less viscous material in the liquid/molten state at the same conditions, hence facilitating the handling and processing of the material, for example when applying it onto a substrate by means of known extrusion or melt coating techniques. Particles having a very low average particle size are also less likely to clog the extrusion nozzle or die. Smaller particles also provide an increased surface to volume ratio compared to larger particles, hence generally enhancing their functionality, i.e., their liquid absorption capability. Particularly, water-insoluble water-swellable absorbent material in particle form provides enhanced absorption capacity and absorption rate when in very small average particle size, owing to the increased surface to volume ratio.

Also, very low average particle size results in a much more homogeneous dispersion of the particulate absorbent material into the inert organic carrier to form the liquid absorbing material of the present invention.

The liquid absorbing material of the present invention in essence allows a safe and easy handling and use of particulate absorbent materials with low and preferably extremely low average particle sizes, in form of dispersions in selected inert hydrophilic organic carriers which are moreover solid at room temperature, hence taking advantage of the benefits related to such small average particle sizes, without the related drawbacks.

The liquid absorbing material according to the present invention can comprise different percentages of its selected components, namely the particulate absorbent material and the inert hydrophilic organic carrier, depending on its final use. The liquid absorbent material may comprise at least about 30% by weight of the inert hydrophilic organic carrier, between about 40% and about 75% by weight, or between about 50% and about 65%. Slightly higher carrier percentages may be desirable for liquid absorbing materials of the present invention where the particulate absorbent material is a liquid gelling material, e.g., chitosan or a derivative thereof, where the carrier may be present in a percentage up to about 70%, about 80%, or about 90% by weight, between about 60% and about 80% by weight.

According to alternative embodiments, the particulate absorbent material can comprise a mixture of different particulate absorbent materials, and/or the inert hydrophilic organic carrier can comprise a mixture of different inert hydrophilic organic carriers, said particulate absorbent materials and said organic carriers each selected as described herein. Typically, the liquid absorbing material of the present invention essentially consists of the particulate absorbent material, or mixture of different particulate absorbent materials having the selected low average particle size described above, and of the inert hydrophilic organic carrier, or mixture of different inert hydrophilic organic carriers, being solid at room temperature. By "essentially consists" is meant that the particulate absorbent material or materials and the inert hydrophilic organic carrier or carriers constitute at least about 90% by weight of the liquid absorbing material of the present invention, at least about 95%, or about 100%.

In general, higher percentages of the inert hydrophilic organic carrier lead to a liquid absorbing material which, in the molten state, has a lower viscosity and is therefore simpler to apply onto a substrate with known low temperature melt coating or melt extrusion techniques. Viscosity in the molten state of the liquid absorbing material of the present invention can be tailored to a desired value more suitable for, e.g., the selected application process and the selected substrate by acting on the choice of the inert hydrophilic organic carrier, and/or of the process temperature, and/or of the carrier percentage, and/or of the average particle size of the particulate material, as can be readily determined by the man skilled in the art.

According to the present invention, particulate absorbent materials comprised in the liquid absorbing material can be synthesized according to known processes such as they have the desired low average particle size. Examples are superabsorbent materials having substantially a spherical shape commercially available from Sumitomo Seika in different average particle sizes under the trade name Aquakeep® 10SH-NF. However, the desired low average particle size may be achieved by suitably grinding a coarser material. Ground particulate absorbent materials, for example, ground superabsorbent materials, are generally cheaper compared to materials directly prepared in the selected average particle size, and are commonly used in absorbent articles. Manufacturing, such as, for example, by grinding, and generally handling particulate materials in low and very low average particle sizes, particularly superabsorbent materials, pose as already explained health and environmental risks, especially when the materials are manufactured in the low and extremely low average particle sizes desirable for the liquid absorbing material of the present invention. One process for making the liquid absorbing material described so far includes providing the selected particulate material, typically in a relatively large average particle size which is easily available in the market and also processed/handled without special care, providing the inert hydrophilic organic carrier which is solid at room temperature, providing the selected inert hydrophilic organic carrier in liquid form by suitably heating it, homogeneously dispersing the selected particulate absorbent material into the selected inert hydrophilic organic carrier in liquid form, thus forming a mixture, and grinding the particulate absorbent material with known means directly within the mixture to the selected average particle size, thus providing the liquid absorbing material of the present invention. Subsequently, the material can be directly applied to a selected substrate and then cooled to regain the solid state, or brought back to solid form by cooling it for further uses, such as storing or shipping. In an alternative embodiment of the process above, the inert hydrophilic organic carrier solid at room temperature can be provided in liquid form by dissolution into a suitable solvent, which should preferably be inert towards the particulate material, and thereafter solidification of the final liquid absorbing material can be obtained by removal of the solvent, e.g., by evaporation.

According to the above process, the particulate absorbent material in low and extremely low average particle size is never present as such, i.e., as a free, dry powder, in any manufacturing step, thus completely avoiding the health and environmental issues related to the handling of particulate absorbent material in very fine average particle size.

EXAMPLE ACCORDING TO THE INVENTION

A liquid absorbing material according to the present invention has the following composition:

| | |
|---|---|
| 55% | PEG 1500, mp 45° C. |
| 45% | Superabsorbent material with average particle size of 15μ |

A particulate superabsorbent material with average particle size of 15μ is prepared by suitably grinding the material available from Nippon Shokubai Co. Ltd. under the trade name Aqualic CA Type L74 to the desired average particle size, e.g., in a Fluid Bed Counter Mill AFG from Hosokawa Alpine. The particles of superabsorbent material are added and uniformly dispersed into a hydrophilic organic carrier which is a polyethylene glycol (M.W. 1500) available from Clariant GmbH under the trade name Polyglykol 1500S provided in liquid state by heating at 70° C.

The average particle size of the superabsorbent material is measured by means of a laser diffraction analysis apparatus model Helos, with dry feeding and dispensing system Rodos, both available from Sympatec GmbH. The average particle size is measured by dry analysis on the particles in dry dispersion. The test is conducted at controlled conditions of 23° C. and 50% relative humidity on the material which has been kept in such conditions for at least 2 hours before the test.

Alternatively, the average particle size can be also measured in the final liquid absorbing material by preparing a liquid suspension for example dissolving at room temperature the solid organic carrier into a suitable solvent which does not interact with the particulate absorbent material. In the case of the material of the example, a liquid suspension can be suitably prepared by dissolving the PEG 1500 containing the particulate absorbent material into a lower molecular weight liquid PEG, e.g., PEG 30, and analyzing the liquid suspension with the Helos analyzer provided with a suitable wet dispersing system also available from Sympatec GmbH.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid absorbing material consisting of a particulate absorbent material and an inert hydrophilic organic carrier, said particulate absorbent material being dispersed into said inert hydrophilic organic carrier, said particulate absorbent material and said inert hydrophilic organic carrier constituting at least 90% by weight of said liquid absorbing material, and said particulate absorbent material having an average particle size of less than about 40µ, wherein said inert hydrophilic organic carrier is water-soluble and solid at room temperature; and wherein the liquid absorbing material has an application temperature of not more than about 110° C.

2. The liquid absorbing material according to claim 1, wherein said inert hydrophilic organic carrier is selected among polyethylene glycol, polypropylene glycol and derivatives thereof.

3. The liquid absorbing material according to claim 1, wherein said particulate absorbent material is a ground material.

4. The liquid absorbing material according to claim 1, wherein said material comprises at least about 30% by weight of said inert hydrophilic organic carrier.

5. The liquid absorbing material according to claim 1, wherein said inert hydrophilic organic carrier is a polyethylene glycol having a molecular weight of at least about 1,200.

6. The liquid absorbing material according to claim 1, wherein said particulate absorbent material is a water-insoluble, water-swellable absorbent material.

7. The liquid absorbing material according to claim 6, wherein said particulate absorbent material is a polyacrylate based superabsorbent material.

8. The liquid absorbing material according to claim 1, wherein said particulate absorbent material includes a liquid gelling material.

9. The liquid absorbing material according to claim 8, wherein said particulate absorbent material includes a chitosan or a derivative thereof.

10. A process for making a liquid absorbing material according to claim 1, said process comprising the following steps:
   providing said particulate absorbent material;
   providing said inert hydrophilic organic carrier in liquid state by melting it or by dissolving it in a suitable solvent;
   homogeneously dispersing said particulate absorbent material in said inert hydrophilic organic carrier forming a mixture;
   grinding said particulate absorbent material into said mixture to the selected average particle size; and
   providing said liquid absorbing material in solid form by cooling or by separating said solvent.

* * * * *